United States Patent
Ekman et al.

(10) Patent No.: US 9,669,170 B2
(45) Date of Patent: Jun. 6, 2017

(54) SAFETY DEVICE AND INJECTION DEVICE

(75) Inventors: Matthew Ekman, Chesire (GB); Christopher James Smith, Cheshire (GB); Troy Baker, Denbighshire (GB); Graham Wilson, Flintshire (GB); Gareth Roberts, Wrexham (GB); Carl Tucker, Conwy (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 458 days.

(21) Appl. No.: 14/241,842

(22) PCT Filed: Sep. 11, 2012

(86) PCT No.: PCT/EP2012/067688
§ 371 (c)(1),
(2), (4) Date: Feb. 27, 2014

(87) PCT Pub. No.: WO2013/037743
PCT Pub. Date: Mar. 21, 2013

(65) Prior Publication Data
US 2014/0213983 A1 Jul. 31, 2014

(30) Foreign Application Priority Data
Sep. 13, 2011 (EP) .................................. 11181037

(51) Int. Cl.
*A61M 5/32* (2006.01)
*A61M 5/28* (2006.01)

(52) U.S. Cl.
CPC .............. *A61M 5/326* (2013.01); *A61M 5/28* (2013.01); *A61M 2005/3247* (2013.01)

(58) Field of Classification Search
CPC . A61M 2005/3247; A61M 5/28; A61M 5/326
See application file for complete search history.

(56) References Cited

U.S. PATENT DOCUMENTS

| 4,935,013 A | 6/1990 | Haber et al. |
| 4,943,281 A | 7/1990 | Kothe |
| 6,261,264 B1 | 7/2001 | Tamaro |
(Continued)

FOREIGN PATENT DOCUMENTS

| EP | 0317518 A1 | 5/1989 |
| FR | 2852851 | 1/2004 |
(Continued)

OTHER PUBLICATIONS

Japanese Office Action in Appl. No. 2014-529020, dated Apr. 12, 2016, 9 pages.

Primary Examiner — Imani Hayman
(74) Attorney, Agent, or Firm — Fish & Richardson P.C.

(57) ABSTRACT

A safety device suitable for a pre-filled syringe containing a medicament includes a chassis adapted to be affixed to the pre-filled syringe, a deformable flexible outer structure made from a material with a shape memory, and a substantially cylindrical needle shield affixed or integral to the outer structure. The deformed flexible outer structure is capable of advancing the needle shield with respect to the chassis in a distal direction into a position in which the needle shield projects from the chassis in the distal direction. A biasing force for advancing the needle shield originates from a shape memory effect that causes the deformed flexible outer structure to substantially return to its unstressed shape.

16 Claims, 2 Drawing Sheets

(56) References Cited

U.S. PATENT DOCUMENTS

| | | |
|---|---|---|
| 6,719,731 B2 | 4/2004 | Parmigiani |
| 8,235,952 B2 | 8/2012 | Wikner |
| 8,845,595 B2 | 9/2014 | Pessin |
| 2004/0267206 A1 | 12/2004 | Rimlinger et al. |
| 2007/0191780 A1 | 8/2007 | Modi |
| 2008/0021409 A1 | 1/2008 | Pessin |

FOREIGN PATENT DOCUMENTS

| | | |
|---|---|---|
| JP | H 02-026563 | 1/1990 |
| JP | 2006/521141 | 9/2006 |
| JP | 2010/521260 | 6/2010 |
| WO | WO 2008/116688 | 2/2008 |

SAFETY DEVICE AND INJECTION DEVICE

CROSS REFERENCE TO RELATED APPLICATIONS

The present application is a U.S. National Phase Application pursuant to 35 U.S.C. §371 of International Application No. PCT/EP2012/067688 filed Sep. 11, 2012, which claims priority to European Patent Application No. 11181037.0 filed Sep. 13, 2011. The entire disclosure contents of these applications are herewith incorporated by reference into the present application.

FIELD OF INVENTION

The present invention relates to safety devices that provide needle safety and more particularly to safety devices for pre-filled syringes. The safety device is adapted to avoid accidental needle pricks and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle, for example needle protector device of EP 0 317 518 A1, retracting mechanism of US 2007/0191780 A1 and safety device of US 2004/0267206 A1.

A different type of safety devices known in the state of the art solves the object of providing needle safety by arranging the pre-filled syringe movable relative to a body, whereas the pre-filled syringe is retracted into the body after the injection.

SUMMARY

It is an object of the present invention to provide an improved safety device for a pre-filled syringe.

It is a further object of the invention to provide an improved injection device comprising a pre-filled syringe that is safe to handle and in particular prevents accidental needle stick injuries.

The object is achieved by a safety device according to claim 1 and by an injection device according to claim 11.

Preferred embodiments of the invention are given in the dependent claims.

In the context of this specification, the terms distal and proximal are defined from the point of view of a person performing an injection. Consequently, a distal direction refers to a direction pointing towards the body of patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device suitable for a pre-filled syringe containing a medicament comprises
a chassis adapted to be affixed to the pre-filled syringe,
a deformable flexible outer structure made from a material with a shape memory and
a substantially cylindrical needle shield affixed or integral to the outer structure.

The deformed flexible outer structure is capable of advancing the needle shield with respect to the chassis in a distal direction into a position in which the needle shield projects from the chassis in the distal direction. A biasing force for advancing the needle shield originates from a shape memory effect that causes the deformed flexible outer structure to substantially return to its unstressed shape.

The safety device is adapted to provide needle safety for a pre-filled syringe retained therein. The flexible outer structure of the safety device provides an alternative biasing means that may be manufactured from inexpensive materials so as to reduce the overall production costs. The safety device is designed as a single use device that is manufactured in high quantities. Furthermore, the outer structure that provides the biasing force to advance the needle shield is disposed during storage and transport in an unstressed state, so that material fatigue is minimized extending the shelf life of the safety device and ensuring a reliable use even after prolonged periods of storage.

Preferably, the flexible outer structure is made from a resilient plastic material with a shape memory. Biasing means made from plastic materials are particularly inexpensive to be produced in high quantities but are in general prone to material fatigue. The safety device of the present invention circumvents this problem by arranging the flexible outer structure in a non-tensioned state. The flexible outer cover is deformed and thus stressed during the injection so that needle safety may be provided by advancing the needle shield that is biased in the distal direction by the deformed outer structure. The shape memory causes the deformed outer structure to return to its original unstressed state, whereby the needle shield is translated distally to cover an injection needle of the pre-filled syringe.

Preferably, the flexible outer structure is made from an inexpensive material like an elastomer or a rubber. The flexible outer structure may cover a substantial part of the exterior surface of the safety device and in particular the parts that are adapted to be touched by a user carrying out the injection. The material of the outer structure may have a texture that enhances gripping of the safety device to facilitate a safe handling during the injection.

In a further embodiment, the thickness of the flexible outer structure varies in axial direction. For example, the ends of the flexible outer structures are thicker than the middle. In particular, elastic elements in the form of arms forming by longitudinal recesses in the flexible outer structure have thick ends and are thin in the middle. Such design with varied dimensions of the flexible outer structure supports deformation and strength of the biasing force of the flexible outer structure.

According to another embodiment, longitudinal recesses of the flexible outer structure have different lengths. In particular, one pair of corresponding longitudinal recesses has a length longer than another pair of corresponding longitudinal recesses or vice versa. Such design supports the deformation and bending outwards of the flexible outer structure during drug delivery.

According to a possible embodiment of the invention, the outer structure provides a grip enhancing and non-slip outer cover for the safety device. This may be achieved by the texture of the plastic material of the flexible outer structure that substantially provides an outer shell for the safety device and, additionally or alternatively, by gripping features like ribs or knobs disposed on the outer surface of the outer structure so as to provide a firm grip of the safety device.

According to another possible embodiment of the invention, at least a proximal section of the flexible outer structure is resiliently deformable and comprises a plurality of longitudinal recesses so as to allow for a deformation of the proximal section. The proximal section is deformed and bent outwards during the drug delivery stage of the injection. After completion of the drug delivery stage, the proximal section of the outer structure relaxes to return to its unstressed state by the memory effect of the material so that needle safety may be provided by advancing the needle shield in the distal direction.

The needle shield and the flexible outer structure may be mounted to the chassis of the safety device by a first clip engaging a first notch arranged on the chassis. The first clip may be in a ramped engagement with the first notch so as to allow for a deflection of the first clips to disengage the first notch when the biasing force provided by the deformed outer structure is applied to the needle shield. The needle shield may thus be translated with respect to the chassis in the distal direction to cover the injection needle so that accidental needle stick injuries may be avoided.

The needle shield is connected to the flexible outer structure. Alternatively, the needle shield is formed by an enforced and strengthened distal section of the flexible outer structure that at least resists an axial deformation so that a re-exposure of the injection needle may be avoided. A second clip may be arranged proximally on the flexible outer structure that is adapted to latch to a second recess arranged on the chassis to couple the deformed and thus stressed flexible outer structure to the chassis so as to bias the needle shield with respect to the chassis in the distal direction.

According to another embodiment of the invention, the outer structure comprises at least one radial projection adapted to be gripped by the user facilitating manual operation of the safety device. In particular two projections may project radially outwards from opposite sides of the outer structure. Alternatively, the projection may be arranged as an annular flange arranged around a circumference of the outer structure of the safety device. The outer structure is manually deformed during the injection to provide the biasing force biasing the needle shield in the distal direction. The biasing force may be counteracted by the user holding the safety device. The needle shield may be advanced upon removal of the safety device from the injection site and release of the projection.

An injection device according to the present invention comprises a pre-filled syringe and a safety device. The pre-filled syringe comprises
 a barrel containing a liquid medicament,
 a plunger translatably disposed within the barrel and
 an injection needle attached to the distal end of the barrel.
The safety device comprises
 a chassis adapted to be affixed to the pre-filled syringe,
 a resiliently deformable flexible outer structure made from a material with a shape memory and
 a substantially cylindrical needle shield connected to the outer structure or arranged with the outer structure as one piece.
At least a section of the flexible outer structure covers parts of the plunger. Alternatively, at least a section of the flexible outer structure is connected to the plunger so that a translation of the plunger in a distal direction to expel the medicament through the injection needle causes deformation of the flexible outer structure. The deformed flexible outer structure is capable of advancing the needle shield with respect to the chassis in a distal direction into a position in which the needle shield covers the injection needle. A biasing force for advancing the needle shield originates from a shape memory effect that causes the deformed flexible outer structure to substantially return to its unstressed shape.

The injection device comprising the pre-filled syringe and the safety device combines the aforementioned advantages and avoids inadvertent needle stick injuries after an injection delivering the medication beneath the skin of patient.

According to a possible embodiment, an opening is provided on the chassis so as to allow for a visual inspection of the pre-filled syringe and its remaining content. The pre-filled syringe may have a scale disposed on its barrel so that the user may inject a defined amount of the medicament initially contained in the pre-filled syringe. Performing partial injections into various injection sites located on different parts of the patient's body minimizes the risk of causing inflammations. This is of particular importance for people suffering from chronic diseases like diabetes that have to perform several injections each day.

As the safe device and the injection device are particularly suited for being used when self-administering the medicament, the person referred to as the user or the patient may be one and the same person.

The flexible outer structure is made from a resilient plastic material that provides an inexpensive biasing means for advancing the needle shield over the distal tip if the injection needle to provide needle safety so that the injection device may be cost-efficiently mass-produced.

Preferably, the plastic material is an elastomer or a rubber that covers substantial parts of the outer surface of the injection device.

The outer structure provides an outer cover for the injection device that comprises grip enhancing features and more particularly non-slip features that improve the grip the user holding the injection device during the injection. The grip enhancing features may in particular be provided by the texture of the plastics material of the outer structure.

A proximal section of the flexible outer structure may be arranged to be resiliently deformed during the drug delivery stage of the injection. The proximal section of the outer structure comprises a plurality of longitudinal recesses so as to allow for a deformation of the proximal section when the user depresses the plunger into the barrel of the pre-filled syringe to dispose the medicament beneath the skin of the patient. The proximal section is deformed and bent outwards so that the proximal section of the outer structure is in a maximum stressed and deformed stage at the end of the injection stroke. The proximal section of the outer structure may thus relax and return to its unstressed state by the shape memory effect of the material, whereby the needle shield is advanced in the distal direction to cover the injection needle.

Furthermore, the outer structure comprises at least one radial projection facilitating manual operation of the injection device during an injection. The at least one radial projection is adapted to be gripped by the user, which facilitates manual operation of the safety device. In particular two projections may project radially outwards from opposite sides of the outer structure. Alternatively, the projection may be arranged as an annular flange arranged around a circumference of the outer structure of the safety device. The projections provide gripping means similar to the ones commonly found on traditional syringes. In particular, the projections are adapted to provide support for an index finger and a second finger when the user's thump presses against the plunger to expel the medicament through the injection needle. The injection device is used to great extent like a standard syringe. However, depression of the plunger into the syringe causes deformation of the flexible outer structure. The user holding the injection device counteracts the biasing force caused by the deformed outer structure. Upon release, the deformed outer structure may relax, whereby then needle shield is translated distally so as to cover the injection needle.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limitative of the present invention, and wherein.

Corresponding parts are marked with the same reference symbols in all figures.

DETAILED DESCRIPTION

Figure 1A:
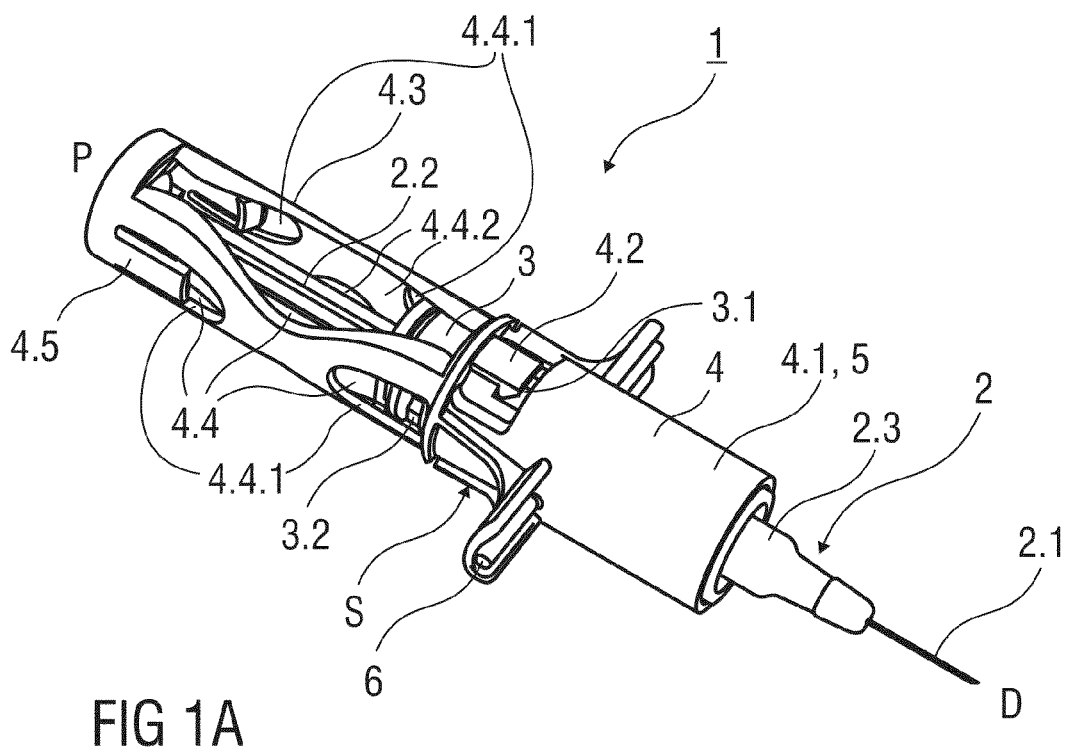
FIGS. 1A and 1B shows an isometric view of an injection device with a flexible outer structure before an injection.
Figure 1B:
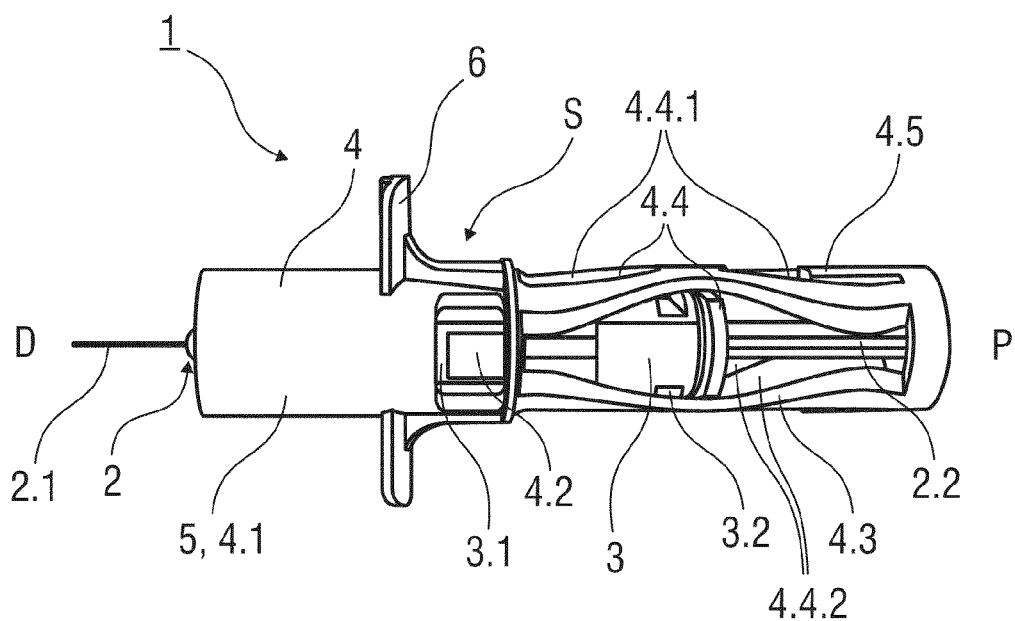

FIGS. 1A and 1B show an injection device 1 before drug delivery in isometric views. The injection device 1 comprises a pre-filled syringe 2 containing a liquid medicament. An injection needle 2.1 is attached to a distal end of the pre-filled syringe 2. A plunger 2.2 is arranged to be depressed into a barrel 2.3 of the pre-filled syringe 2 in a distal direction D to expel the medicament contained therein through the injection needle 2.1.

A safety device S comprises a chassis 3, a flexible outer structure 4 and a needle shield 5. The chassis 3 is affixed to the barrel 2.3 of the pre-filled syringe 2. The cylindrical needle shield 5 consists of a reinforced tubular distal section 4.1 of the flexible outer structure 4 that resists at least an axial deformation so as to prevent a re-exposure of the injection needle 2.1 when covered by the needle shield 5 to provide needle safety after an injection. Alternatively, the needle shield 5 may be made from a relative stiff plastic material that is attached to and covered by the distal section 4.1 of the flexible outer structure 4.

The flexible outer structure 4 comprises first clips 4.2 that latch into a corresponding first notch 3.1 formed into the chassis 3 to mount the needle shield 5 to the chassis 3.

The flexible outer structure 4 is made from a flexible and resilient plastic material with a shape memory. In particular, the flexible outer structure 4 may be made from an elastomer or rubber. The flexible outer structure 4 of the safety device S provides a resilient biasing means for biasing the needle shield 5 in the distal direction D at the end of an injection so as to translate the needle shield 5 distally to cover the injection needle 2.1. The flexible outer structure 4 is resiliently deformed when the plunger 2.2 is depressed into the barrel 2.3 of the pre-filled syringe 2. The energy stored during the deformation is then used to translate the needle shield 5 distally to cover the injection needle 2.1, whereby the flexible outer structure 4 essentially returns to its original shape by an effect of material memory.

Further, the thickness of the flexible outer structure 4 varies in axial direction as it is best shown in FIGS. 1A, 1B. For example, the ends of the flexible outer structure 4 are thicker than the middle.

A proximal section 4.3 of the flexible outer structure 4 extends over the plunger 2.2 and comprises a plurality of longitudinal recesses 4.4 to allow for a resilient deformation of the proximal section 4.3 when the plunger 2.2 is pushed in the distal direction D to expel the medicament.

In particular, the longitudinal recesses 4.4 form elastic elements in the form of arms in the flexible outer structure 4. The arms have thick ends and are thin in the middle. Such design with varied dimensions of the thickness of the flexible outer structure 4 supports deformation and strength of the biasing force.

The longitudinal recesses 4.4 have different lengths. In particular, one pair 4.4.1 of corresponding longitudinal recesses 4.4 has a length shorter than another pair 4.4.2 of corresponding longitudinal recesses 4.4 or vice versa. Such design supports the deformation and bending outwards of the flexible outer structure 4 during drug delivery.

Two projections 6 protrude from opposite sides of the flexible outer structure 4 in a radial direction to provide a gripping means adapted to support the fingers of a user of the injection device 1 during an injection.

Additionally, the outer structure 4 provides an outer cover for the safety device S and thus the injection device 1. The material of the outer structure 4 may provide a texture that enhances the grip of the user holding the injection device 1 during an injection. In particular, the material of the outer structure 4 may be relatively soft so as to avoid slipping when the injection is carried out.

The needle shield 5 is only touched by fingers which touch both flanges of the projections 6. For this reason it could be alternatively advantageous to have small cavities, e.g. two cavities, under the flange instead of a texture.

A second clip 4.5 is arranged at a proximal end of the proximal section 4.3 of the flexible outer structure 4. The second clip 4.5 is adapted to latch into a corresponding second notch 3.2 of the chassis 3 to couple the deformed and stressed proximal section 4.3 to the chassis 3 so as to bias the needle shield 5 in the distal direction D.

Figure 2:
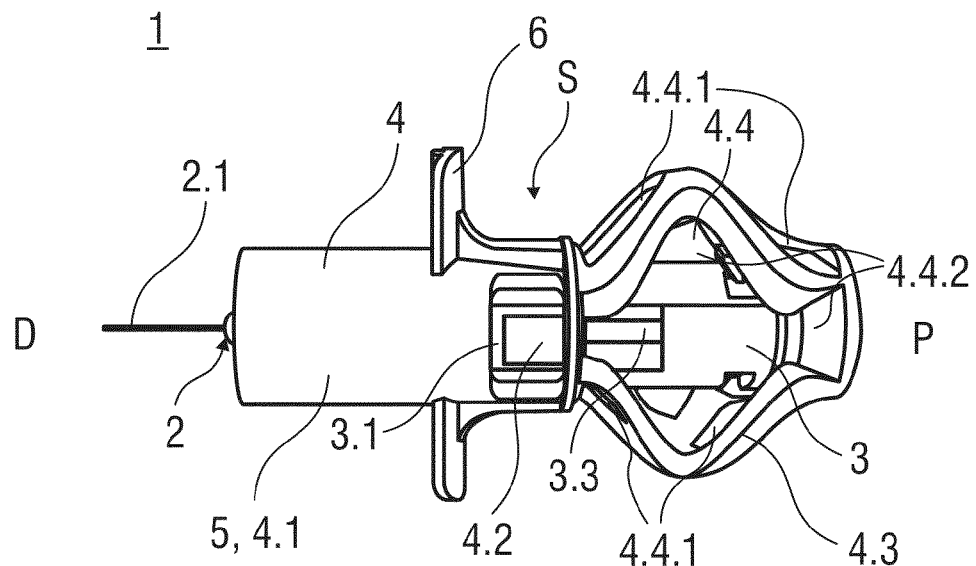
FIG. 2 shows an isometric view of the injection device with the flexible outer structure deformed and stressed.

FIG. 2 shows an isometric view of the injection device 1 after the medicament has been disposed beneath of the patient receiving the injection. The plunger 2.2 is completely depressed into the barrel 2.3 of the pre-filled syringe 2. The proximal section 4.3 of the flexible outer structure 4 is deformed and bent radial outwards.

The second clip 4.5 located at the proximal end of the proximal section 4.3 of the flexible outer structure 4 engages the second notch 3.2 arranged on the chassis 3. The deformed and stressed flexible outer structure 4 thus biases the chassis 3 and the needle shield 5 away from each other. This biasing force is counteracted by the user holding the injection device 1. Upon release, the needle shield 5 is translated distally to surround the injection needle 2.1.

Figure 3:
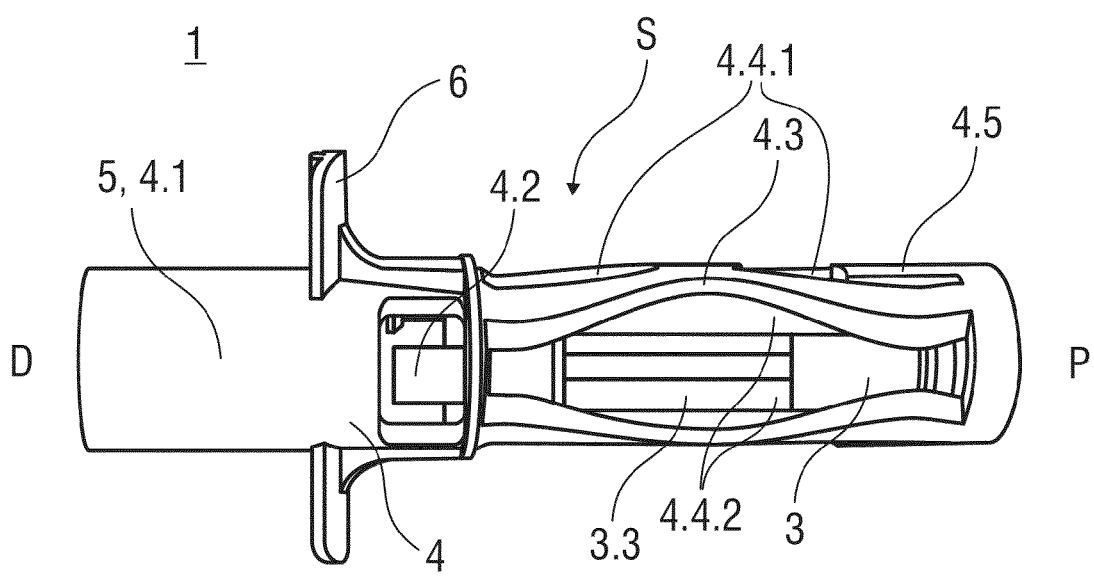
FIG. 3 shows an isometric view of the injection device in a needle safe state.

FIG. 3 shows the injection device 1 in a needle safe state after the injection is completed. The flexible outer structure 4 returned to its non-deformed state by an effect of shape memory. The needle shield 5 is in an advanced position and surrounds the injection needle 2.1. The first clip 4.2 latches to a distal end of the chassis so as to block a translation of the needle shield 5 with respect to the chassis 3 in a proximal direction P. Thus, a re-exposure of the injection needle 2.1 is prevented.

As best seen in FIG. 3, an opening 3.3 may be arranged on the chassis 3 so that the pre-filled syringe 2 and its remaining content are visible to the user performing the injection.

The injection device 1 is operated by the user in a way similar to the one a traditional syringe is used: in particular, the two projections 6 support the index and the middle finger of the user when the thumb is pressed against the proximal end of the plunger 2.2 so as to depress the plunger 2.2 into the barrel 2.3 and expel the medicament through the injection needle 2.1.

A proximal end of the proximal section 4.3 is attached to the proximal end of the plunger 2.2 so that proximal section 4.3 of the flexible outer structure 4 is bent outwards and deformed when the plunger 2.2 is translated distally. When the plunger 2.2 is fully depressed into the barrel 2.3 at the end of the injection stroke, the deformed proximal section 4.3 of the flexible outer structure 4 is latched to chassis 3 by the second clip 4.5 engaging the second notch 3.2. The needle shield 5 is thus advanced distally when the stressed and deformed flexible outer structure 4 returns to its unstressed state by the shape memory effect. The flexible outer structure 4 thus provides a biasing means for providing needle safety that is stressed during use of the injection device 1, whereas the flexible outer structure 4 is stored before and after the injection in an unstressed state to avoid material fatigue and to extend the shelf-life of the injection device 1.

The invention claimed is:

1. A safety device suitable for a pre-filled syringe containing a medicament comprising
   a chassis adapted to be affixed to the pre-filled syringe,
   a flexible outer structure made from a material with a shape memory and
   a substantially cylindrical needle shield affixed or integral to the flexible outer structure, wherein when deformed, the flexible outer structure is capable of advancing the needle shield with respect to the chassis in a distal direction into a position in which the needle shield projects from the chassis in the distal direction and wherein a biasing force for advancing the needle shield originates from a shape memory effect that causes the deformed flexible outer structure to substantially return to an unstressed shape of the outer structure,
   wherein the flexible outer structure is adapted to cover the pre-filled syringe with a plunger and to provide a grip enhancing and non-slip outer cover and wherein a clip arranged proximally on the flexible outer structure is adapted to latch to a notch arranged on the chassis to couple the deformed flexible outer structure to the chassis so as to bias the needle shield with respect to the chassis in the distal direction.

2. The safety device according to claim 1, wherein the flexible outer structure is made from a resilient plastic material.

3. The safety device according to claim 2, wherein the plastic material comprises an elastomer or a rubber.

4. The safety device according to claim 1, wherein a thickness of the flexible outer structure varies in axial direction.

5. The safety device according to claim 1, wherein a proximal section of the flexible outer structure comprises a plurality of longitudinal recesses so as to allow for a deformation of the proximal section.

6. The safety device according to claim 5, wherein the longitudinal recesses has different lengths.

7. The safety device according to claim 5, wherein one pair of corresponding longitudinal recesses has a length shorter than another pair of corresponding longitudinal recesses.

8. The safety device according to claim 1, wherein the needle shield and the flexible outer structure is mounted to the chassis by a first clip engaging a first notch arranged on the chassis so as to allow for a translation of the needle shield with respect to the chassis in the distal direction.

9. The safety device according to claim 1, wherein the flexible outer structure comprises at least one radial projection facilitating manual operation of the safety device (S).

10. An injection device comprising a pre-filled syringe and a safety device, wherein the pre-filled syringe comprises
    a barrel containing a liquid medicament,
    a plunger translatably disposed within the barrel and
    an injection needle attached to the distal end of the barrel
        and wherein the safety device comprises
    a chassis adapted to be affixed to the pre-filled syringe,
    a flexible outer structure made from a material with a shape memory and a substantially cylindrical needle shield,
    wherein translation of the plunger in a distal direction to expel the medicament through the injection needle causes deformation of the flexible outer structure, wherein when deformed, the flexible outer structure is capable of advancing the needle shield with respect to the chassis in a distal direction into a position in which the needle shield covers the injection needle and wherein a biasing force for advancing the needle shield originates from a shape memory effect that causes the deformed flexible outer structure to substantially return to an unstressed shape, wherein the flexible outer structure is adapted to cover the pre-filled syringe with a plunger and to provide a grip enhancing and non-slip outer cover and wherein a clip arranged proximally on the flexible out structure is adapted to latch to a notch arranged on the chassis to couple the deformed flexible outer structure to the chassis so as to bias the needle shield with respect to the chassis in the distal direction.

11. The injection device according to claim 10, wherein an opening is provided on the chassis so as to allow for a visual inspection of the pre-filled syringe and remaining content of the pre-filled syringe.

12. The injection device according to claim 10, wherein the flexible outer structure is made from a resilient plastic material.

13. The injection device according to claim 12, wherein the plastic material comprises an elastomer or a rubber.

14. The injection device according to claim 10, wherein a thickness of the flexible outer structure varies in the axial direction.

15. The injection device according to claim 10, wherein a proximal section of the flexible outer structure comprises a plurality of longitudinal recesses so as to allow for a deformation of the proximal section.

16. The injection device according to claim 10, wherein the outer structure comprises at least one radial projection facilitating manual operation of the injection device during an injection.

* * * * *